United States Patent
Phillips et al.

(10) Patent No.: US 7,591,788 B2
(45) Date of Patent: Sep. 22, 2009

(54) ADAPTIVE CONTRAST AGENT MEDICAL IMAGING

(75) Inventors: Patrick J. Phillips, Sunnyvale, CA (US); Ismayil Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 227 days.

(21) Appl. No.: 10/644,862

(22) Filed: Aug. 19, 2003

(65) Prior Publication Data
US 2005/0055178 A1 Mar. 10, 2005

(51) Int. Cl.
*A61B 8/14* (2006.01)

(52) U.S. Cl. .................. 600/458; 600/437; 600/443; 600/447

(58) Field of Classification Search ......... 600/437–472; 424/9.51, 9.52; 128/916; 367/7, 11, 130, 367/138; 73/625, 626
See application file for complete search history.

(56) References Cited

U.S. PATENT DOCUMENTS

| | | | | |
|---|---|---|---|---|
| 5,469,849 | A * | 11/1995 | Sasaki et al. ............... | 600/443 |
| 5,577,505 | A * | 11/1996 | Brock-Fisher et al. ...... | 600/458 |
| 5,675,554 | A | 10/1997 | Cole et al. | |
| 5,873,829 | A * | 2/1999 | Kamiyama et al. ......... | 600/443 |
| 6,010,456 | A * | 1/2000 | Rhyne ........................ | 600/447 |
| 6,045,506 | A * | 4/2000 | Hossack ..................... | 600/443 |
| 6,050,944 | A * | 4/2000 | Holley et al. ............... | 600/441 |
| 6,168,565 | B1 * | 1/2001 | Napolitano ................. | 600/447 |
| 6,210,334 | B1 | 4/2001 | Phillips | |
| 6,213,947 | B1 | 4/2001 | Phillips | |
| 6,340,348 | B1 * | 1/2002 | Krishnan et al. ........... | 600/447 |
| 6,436,041 | B1 | 8/2002 | Phillips et al. | |
| 6,461,303 | B2 * | 10/2002 | Angelsen ................... | 600/458 |
| 6,494,841 | B1 | 12/2002 | Thomas et al. | |
| 6,497,666 | B1 | 12/2002 | Phillips et al. | |
| 6,500,122 | B1 * | 12/2002 | Washburn et al. .......... | 600/443 |
| 6,503,203 | B1 * | 1/2003 | Rafter et al. ................ | 600/458 |
| 6,579,238 | B1 | 6/2003 | Simopoulos et al. | |
| 6,612,989 | B1 * | 9/2003 | Brock-Fisher ............. | 600/447 |

(Continued)

FOREIGN PATENT DOCUMENTS

EP 1281368 A2 * 2/2003

OTHER PUBLICATIONS

"Optimized Receive Filters and Phase-Coded Pulse Sequences for Contrast Agent and Nonlinear Imaging," by W. Wilkening, B. Brendel, H. Hiang, J. Lazenby and H. Ermert; 2001 IEEE Ultrasonics Symposium; pp. 1733-1737.

*Primary Examiner*—Long V Le
*Assistant Examiner*—Sanjay Cattungal

(57) ABSTRACT

System parameters for contrast agent medical imaging are conveniently set. A simplified contrast agent configuration is provided. One contrast agent imaging mode or configuration is dynamically determined and optimized based on the user's selected transmit level and/or a real-time measurement of the contrast agent signals. A simplified user interface provides one contrast agent imaging mode without a need to switch between multiple modes or contrast agent detection techniques and associated contrast agent imaging parameters. The contrast agent detection technique and imaging parameters are adjusted or selected based on changes in the transmit levels for contrast agent imaging. Appropriate contrast agent detection techniques and imaging parameters are selected for each given transmit level without the user having to switch the mode or configuration of the system during an imaging session.

10 Claims, 2 Drawing Sheets

U.S. PATENT DOCUMENTS

| | | |
|---|---|---|
| 6,626,836 B2 | 9/2003 | Mao et al. |
| 6,632,177 B1 | 10/2003 | Phillips et al. |
| 6,679,844 B2 | 1/2004 | Loftman et al. |
| 6,786,869 B2 * | 9/2004 | Hashimoto .................. 600/437 |
| 6,858,008 B2 * | 2/2005 | Li et al. ...................... 600/437 |
| 6,899,681 B1 * | 5/2005 | Phillips et al. .............. 600/458 |
| 7,074,186 B2 * | 7/2006 | Loftman et al. ............. 600/437 |
| 2003/0236459 A1 * | 12/2003 | Loftman et al. ............. 600/437 |
| 2004/0087857 A1 * | 5/2004 | Napolitano et al. ......... 600/443 |
| 2004/0204649 A1 * | 10/2004 | Ramraj et al. ............... 600/437 |
| 2008/0228070 A1 | 9/2008 | Phillips et al. |

* cited by examiner

ADAPTIVE CONTRAST AGENT MEDICAL IMAGING

BACKGROUND

This present invention relates to contrast agent imaging. In particular, contrast agent imaging in medical imaging systems is enhanced.

The use of contrast agents in routine clinical examinations has become more common. Despite initial apprehension concerning the need for an IV to inject the contrast agents, the clinical benefits may be significant. With improvements in detection techniques by equipment manufacturers and more stable agents by pharmaceutical companies, the number of successful examinations with contrast agents is growing. However, contrast agent imaging in clinical examinations may be overly complex due to the large number of detection techniques, difficulty of optimum adjustment and poor user interface.

Many equipment manufacturers have introduced numerous contrast agent techniques for imaging contrast agents. The following is an example list illustrating some of the multiple imaging modes or techniques available: Phase Inversion, Pulse Inversion, Power Pulse Inversion (PPI), Ensemble Contrast Imaging (ECI), Power Harmonics, Power Angio, Power Modulation (PM), Ultraharmonics, Flash Echo Imaging, Advanced Dynamic Flow, 1.5 Harmonic Imaging, Coherent Contrast Imaging (CCI), Contrast Pulse Sequencing (CPS), Power Contrast Imaging (PCI), and Agent Detection Imaging (ADI). Some differences among these imaging modes and techniques include the use of high power imaging or low power imaging, the types of transmitted pulses, the number of transmitted pulses per line in an image, the type of filtered received frequency content, and the type of filtering across all received pulses. These differences offer opportunities for adjusting performance by the user. However, deciding which option is most appropriate can be complicated. Even with successful marketing and educational materials, the opportunity still exists that an inappropriate technique, or improper machine settings (or preset values), may be used, generating suboptimal results.

Another complication for efficient contrast agent imaging examination is setting the acoustic transmit power level. The Mechanical Index (MI) is often used as a primary index, or only index, for setting the imaging condition based on transmitted power before and after contrast administration. This index is a single number that represents peak negative pressure normalized by frequency at a single point in three-dimensional space. Many users assume this number is the value at the electronic focus. However, this assumption can be incorrect for specific imaging conditions. The MI is not a comprehensive measure relating to the best imaging setting.

Given the evolution of technologies and continued introduction of new contrast agent imaging detection techniques, ultrasound companies have been challenged to create and market a simple package for contrast agent imaging. In addition to multiple detection modes, the user interfaces have not all been easy to use. Users typically select a specific configuration for contrast agent imaging from a menu structure of multiple applications or contrast agent imaging techniques. In response to the configuration, a particular contrast agent detection technique and associated transmit sequence is selected. Other contrast agent imaging parameters are also set and maintained until a different configuration is selected by the user.

Users that do not achieve the expected imaging performance after starting with a preset system setting or Mechanical Index often operate a transmit level adjustment and vary the transmit level until the imaging performance is improved. While the pre-detection gains may be adjusted due to the different transmit level, other internal contrast agent system parameters specific to a selected detection technique do not change as the transmit level varies. The contrast agent detection technique does not change when the transmit level is altered. Suboptimal contrast agent imaging may result.

BRIEF SUMMARY

The present invention is defined by the following claims, and nothing in this section should be taken as a limitation on those claims. By way of introduction, the preferred embodiments described below include a method and systems for setting parameters for contrast agent medical imaging. A simplified contrast agent configuration is provided where an appropriate contrast agent detection technique and/or contrast agent imaging parameters are achieved consistently and more often then exists with current methods. Examination workflow is improved for contrast agent studies by offering one contrast agent imaging mode or configuration that is dynamically determined and optimized based on the user's selected transmit level and/or a real-time measurement of the contrast agent signals.

A simplified user interface provides one contrast agent imaging mode without a need to switch between multiple modes or contrast agent detection techniques and associated contrast agent imaging parameters. The contrast agent detection technique and imaging parameters are adjusting or selected based on changes in the transmit levels for contrast agent imaging. Either a single user input control or real time measurements are used to select a transmit level, resulting in automatic selection of adjustment of the detection technique and/or imaging parameters. Appropriate contrast agent detection techniques and imaging parameters are selected for each given transmit level without the user having to switch the mode or configuration of the system during an imaging session. As a result, contrast agent examinations are simplified while minimizing suboptimal selection by a user.

In a first aspect, a method for setting parameters for contrast agent medical imaging is provided. A transmit level is set. A setting for at least one contrast agent imaging parameter is automatically selected as a function of the transmit level. The contrast agent imaging parameter is one of the group of: transmit sequence, detection technique, transmit modulation frequency, transmit bandwidth, transmit coding, number of transmit foci per scan line, number of transmit pulses per scan line, number of scan lines per image, time between transmissions, velocity scale, reverberation-suppression pulses, receive bandwidth, receive demodulation frequency and combinations thereof.

In a second aspect, a method for setting parameters for contrast agent medical imaging is provided. Automatically adjustment from a first contrast agent detection technique to a second contrast agent detection technique is provided. The first contrast agent detection technique is different than the second contrast agent detection technique. The adjustment is performed in response to a change in a transmit level.

In a third aspect, a method for setting parameters for contrast agent medical imaging is provided. A system is configured for contrast agent imaging. A transmit level and transmit sequence are altered for the contrast agent imaging in response to a single user input control. At least two different transmit levels are associated with at least one of the transmit sequences.

In a fourth aspect, a system for adaptively setting parameters for contrast agent medical imaging is provided. A memory is operable to store a table of a plurality of transmit sequences and a plurality of transmit levels. At least two transmit levels are associated with at least one of the transmit sequences. A processor is operable to select different ones of the plurality of transmit sequences and of the plurality of transmit levels in response to a single input from a user input control.

Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A simplified user interface provides one contrast agent imaging mode without a need to switch between multiple modes during an imaging session. A typical imaging session includes the injection of contrast agents and about five to thirty minutes of imaging. If the user is initially dissatisfied with the imaging results, the user adjusts the transmit level. Alternatively, the system automatically determines an optimal transmit level as contrast agent imaging is performed. Rather than just changing the gain, various contrast agent imaging parameters are changed in response to the altered transmit level. The contrast agent detection technique, such as the transmit sequence and associated combination of echo signals on receive, and/or other contrast agent imaging parameters are adjusted or selected based on changes in the transmit levels. Appropriate contrast agent detection techniques and imaging parameters are selected for each given transmit level without the user having to switch the modes or configuration of the system during the imaging session. As a result, contrast agent examinations are simplified while increasing optimal contrast agent imaging.

Figure 1:
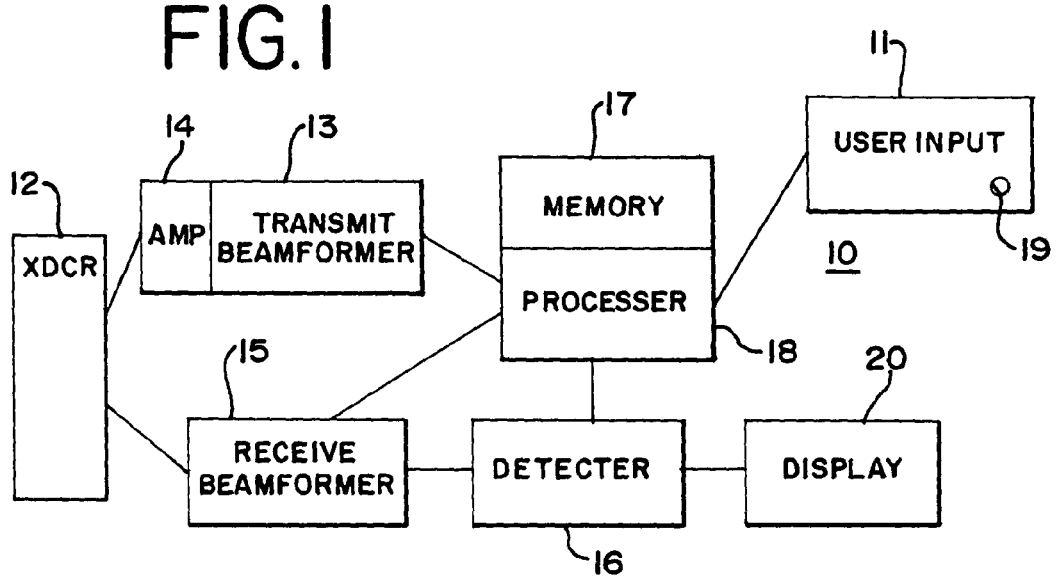
FIG. 1 is a block diagram of one embodiment of an ultrasound contrast agent imaging system.

FIG. 1 shows a system 10 for setting parameters for contrast agent medical imaging. The system 10 includes a user input 11, a transducer 12, a transmit beamformer 13 with a transmit amplifier 14, a receive beamformer 15, a detector 16, a memory 17, a processor 18 and a display 20. Additional, different or fewer components may be provided, such as including multiple detectors associated with contrast agent, B-mode and flow or Doppler imaging. As another example, a scan converter is provided to format the acquired polar coordinate data into data in a Cartesian coordinate format for the display. The system 10 is a medical diagnostic ultrasound system from any of various manufacturers with one or more contrast agent detection techniques.

The user input 11 is a keyboard, mouse, trackball, touch screen, dedicated keys, programmable keys, sliders, rocker switches, rotatable knobs and any other now known or later developed user input device. In one embodiment, a single user input control, such as a rotatable knob, a rocker switch, a touch screen control or a level push button to be held "on" for time period or other control, is used for controlling contrast agent imaging. Where the system is configured using a menu structure or activation of the user input control for contrast agent imaging, the single user input control is used for adjusting the transmit power level and other contrast agent imaging parameters. For example, as the rotatable knob is rotated, different transmit power levels are selected. Different contrast agent detection techniques and/or imaging parameters are adjusted or selected automatically in response to the new transmit power level. In alternative embodiments, a plurality of controls are provided for adjusting the transmit level, the contrast agent detection technique and/or contrast agent imaging parameters. In yet other alternative embodiments, the system 10 automatically determines the various settings in response to configuring the system 10 for contrast agent imaging.

The transducer 12 is a single element or multiple elements of piezoelectric material. In alternative embodiments, the transducer 12 comprises capacitive membrane structures. For multiple elements, the transducer 12 is a linear, curved linear or multidimensional array. Other transducers for converting between electrical and acoustic energy can be used. The transducer 12 outputs acoustic waveforms at powers set by the transmit amplifier 14. The acoustic waves are transmitted along one or more scan lines in response to settings of the transmit beamformer 13. The transmitted waves have amplitudes, phases, center frequencies, bandwidth, coding and foci also set by the transmit beamformer 13. The number of times the acoustic waveforms are transmitted along a given scan line and pulse repetition interval is also set by the transmit beamformer 13.

The transmit beamformer 13 includes one or more waveform generators, sample memories, oscillators, delays, phase rotators, filters, transmit amplifiers 14, digital-to-analog converters, other digital components, analog components and any other now known or later developed transmit beamformer components. The transmit beamformer 13 is configured into one or more channels for generating one or more electrical waveforms with relative delays and apodization for scanning a region of a patient. The waveforms of each channel have an amplitude, relative phase as compared to other waveforms of other channels or of the same channel at a different time, center frequencies, bandwidth (e.g., number of cycles and type of waveform) and coding (e.g. chirp or no chirp for frequency coding). The relative delays and apodization of the waveforms across the various channels provides for one or more foci along a given scan line or across multiple scan lines for a given transmit event or for sequential transmit events. The waveforms are generated for transmissions along one or more scan lines in response to settings of the transmit beamformer 13. The number of times the acoustic waveforms are transmitted along a given scan line and pulse repetition interval is also set by the transmit beamformer 13.

The transmit amplifier 14 connects with the transducer 12 and is a variable amplifier, digital-to-analog converter or other analog or digital device for changing or increasing a power, peak voltage or other power characteristic of a transmit waveform. In alternative embodiments, the transmit amplifier 14 comprises a voltage divider or other device for reducing the power associated with the transmit waveform. A separate transmit amplifier 14 is provided for each transmit beamformer channel or transducer element, but one transmit amplifier 14 may be used for a plurality of channels or elements. In one embodiment, the transmit amplifier 14 applies apodization for transmitting along a beam and is included as part of a transmit beamformer 13, such as disclosed in U.S. Pat. No. 5,675,554, the disclosure of which is incorporated herein by reference.

The transmit waveforms output from the transmit amplifier 14 are converted to acoustic energy by the transducer 12. Echo signals responsive to the acoustic energy and any contrast agents are received by the transducer 12. The transducer 12 converts the echo signals into electrical signals or data. As used herein, data includes one or more digital samples or analog information. The echo signals are provided to the receive beamformer 15.

The receive beamformer 15 includes amplifiers, channel filters, phase rotators, multipliers, analog-to-digital converters, summers, post-sum filters, memories, buffers, demodulator, digital components, analog components and any other now known or later developed receive beamformer components. The receive beamformer 15 is configured into one or more receive channels connected with one or more transducer elements. The receive channels apply relative delays, apodization and weighting as a function of channel for focusing along the scan lines. The receive channel data is summed together to form beamformed data. Using filters in the channel or after the summer, the bandwidth of the data is adjusted. The demodulator demodulates to one or more receive frequencies, such as fundamental, fractional harmonics (e.g., 1.5 harmonic), second harmonic or other harmonics of the fundamental transmitted frequency. The receive pre-detection gain, such as the dynamic range, noise floor and other gain adjustments are also implemented by the receive beamformer 15.

The detector 16 is a loss of correlation detector, B-mode detector, Doppler detector, flow detector or other contrast agent detector. Any of the contrast agent detection techniques described above may be used. In one embodiment, the detector 16 is used for imaging contrast agents as well as B-mode and F-mode detection. Alternatively, the detector 16 is used for contrast agent detection separate from other detectors for other types of imaging. The detector 16 detects signals responsive to contrast agents, such as fundamental or harmonic signals, contrast agent destruction, loss of correlation due to flow or destruction, or other now known or later developed contrast agent detection technique.

In one embodiment, the detector 16 detects the fundamental, harmonic or fractional harmonic response of the contrast agents. The received signals are filtered or combined (e.g., subtraction, addition, or weighted addition/subtraction of signals from multiple pulses) to isolate the information at the desired pass bands. The envelope or intensity of echo signals, the energy from a flow or Doppler processor or other technique is used to detect the response from the filtered received signals.

In another embodiment, the received signals are responsive to transmissions along the same or adjacent scan lines with different phases, such as two or more transmissions with 180 degree phase shifts. The detector 16 combines signals representing a same or adjacent scan line by addition or subtraction. Equal or different weights may be applied to the signals prior to combination. The envelope or intensity, the energy from a flow or Doppler processor or other technique is used to detect the response from the combined received signals.

In yet another embodiment, the received signals are responsive to transmissions along same or adjacent scan lines with different amplitudes. The received signals may or may not also be associated with different phases, such as 180, lesser or greater shifts, for one or more received lines. The detector 16 is operable to combine the received signals using equal or unequal weights, such as with a finite impulse response filter. The envelope or intensity, the energy from a flow or Doppler processor or other technique is used to detect the response from the combined received signals.

In another embodiment, the received signals are responsive to two or more transmissions along same or adjacent scan lines with a same amplitude and/or phase. When contrast agents are destroyed or disrupted during two or more different transmit events, the received data have a loss-of-correlation (LOC). The second data is different than the first data. In one embodiment, three separate identical waveforms may be transmitted. Fewer or a greater number of pulses can be used for each detected datum. The detector 16 is operable to weight the received data, such as with a [1 −2 1] filter. The envelope or intensity, the energy from a flow or Doppler processor or other technique is used to detect the response from the combined received signals.

Other loss of correlation detection sequences are possible. For example, many sequences used for traditional color flow imaging provide loss of correlation detection in addition to detection of motion (correlated or partially correlated). Sequences that detect motion with imaging modes such as color Doppler velocity (CDV) or color Doppler energy (CDE) also detect loss of correlation. Detectable energy or velocity originates from differences between two or more pulses. Other methods using two or more receive pulses after two or more pulses are transmitted can be used.

Contrast agent detection techniques may be based upon detecting an increase in signal strength or a decrease in signal strength. When contrast agents are destroyed by one pulse, a second pulse may not echo from any contrast agent. The returned signal is less for the second pulse. Conversely, when some contrast agents are disrupted, an encapsulating shell cracks and releases an inner gas. This inner gas can be more reflective than the shell, returning a signal that is stronger. In one embodiment, the detector 16 detects contrast agent from one or more received signals after pulses are transmitted for destroying the contrast agent.

The memory 17 is a look-up table, a RAM, a ROM, a removable storage media, a hard drive or other now known or later developed memory device. The memory 17 is operable to store a table of a plurality of transmit sequences and a plurality of transmit levels. As discussed above, various transmit sequences are used for various contrast agent detection techniques. Each transmit sequence includes a number of pulses (e.g., 1-N), a phase of each of the pulses (e.g., 0–359 degrees) and an amplitude of each of the pulses (e.g., same or different—[0.5 1 0.5]) for each scan line.

Two or more transmit levels, including multiple ranges of transmit levels, may be associated with one or more of the transmit sequences. Different transmit power levels are associated with a same or different transmit sequences and associated contrast agent detection techniques. For example, a transmit sequence of pulses with interpulse amplitude and/or phase modulation for each of a plurality of scan lines can be transmitted with one or more peak transmit levels per transmit sequence. As an example, a transmit sequence of [1 −2 1] or [1 −1], where the numerical value represents a peak weight or amplitude and the minus sign represents a 180 degree phase shift, is transmitted at a maximum transmit level or multiple lower transmit levels. For each of the multiple transmit levels, the peak transmit level between the pulses in the sequence is maintained. Similarly, a transmit sequence of pulses with a same amplitude and phase for each of the plurality of scan lines (e.g., [1 1] or [1 1 1]), is transmitted at multiple peak transmit levels for the sequence. The change in transmit level for the sequence occurs after the sequence is transmitted and can be between firings associated with a line in an image or between frames containing multiple lines of an image.

The processor 18 is one or more of an application specific integrated circuit, a general processor, a digital signal processor, a control processor or other device operable to select different ones of the plurality of transmit sequences and of the plurality of transmit levels in response to a single input from the user input control or in response to an automatic measurement. For example, the processor 18 is operable to obtain a measure of contrast agent response and automatically select a different one of the plurality of transmit sequences and of the plurality of transmit levels in response to the measure. in response to user input initiating automatic transmit power setting or in response to software, the processor 18 determines the contrast agent imaging transmit power as a function of a comparison of sequentially acquired first and second data. The processor 18 compares sequentially acquired first and second detected data, such as loss of correlation detected data, to determine a transmit power associated with destruction or non-destruction of contrast agent. The comparison and setting of the contrast agent imaging transmit power is performed automatically by the processor 18. User input to initiate or override the automatic setting may be provided. Such processes are taught, for example, in U.S. Pat. No. 6,899,681; the disclosure of which is incorporated herein by reference.

As another example, the user adjusts the transmit level or provides an input indicating a change for contrast agent imaging, so the processor 18 alters the contrast agent imaging parameters. As the user activates a single control, such as rotating a knob, the processor 18 is operable to select from a range of transmit levels and at least two different transmit sequences.

The processor 18 is connected with or includes the table of the memory 17. The table includes settings for a subset of or each of the transmit levels, transmit modulation frequency, transmit bandwidth, transmit coding, number of transmit foci per scan line, number of transmit pulses per scan line, number of scan lines per image, time between transmissions, velocity scale, reverberation-suppression pulses, receive bandwidth, receive demodulation frequency and/or other contrast agent imaging parameters. The processor 18 accesses the table to set one or more of the contrast agent imaging parameters and control the appropriate component for implementing the setting.

One exemplary table is provided below (table 1). Two, three or more transmit levels may be provided. In one embodiment, the table includes all possible setting combinations. In other embodiments, the table includes a sub-set of the combinations and other combinations are interpolated or extrapolated from the table. In yet another embodiment, the table includes ranges of settings usable together.

As an example, the table includes three transmit levels, such absolute transmit levels of low (e.g., 0.15 MI), medium (e.g., 0.6 MI) and high (e.g., 1.9 MI) or a range for each group of transmit levels (e.g., 0.1–0.3; 0.4–1.0 and 1.1–1.9). For the low transmit level, the processor 18 is operable to select settings of the transmit sequence having multiple pulses with at least one of different amplitudes and phases and at least one of (i) the transmit modulation being low and (ii) the receive demodulation frequency being medium. For medium transmit level, the processor 18 is operable to select the transmit sequence having multiple pulses with at least one of different amplitudes and phases and at least one of (i) the transmit modulation being medium and (ii) the receive demodulation frequency being high. For a high transmit level, the processor 18 is operable to select the transmit sequence having multiple pulses with all pulses having one of a same amplitude and a same phase and at least one of (i) the transmit modulation being high and (ii) the receive demodulation frequency being low. The high, medium and low are intended to be relative terms based on specific systems, type of contrast agents, transducer 12 frequency response and other frequency related variables. A lower transmit frequency modulation with a higher receive demodulation indicates either harmonic (e.g., 1.5 or second harmonic) receive or a relative frequency as compared to other frequencies (e.g. still receiving primarily or including the fundamental frequencies). Once the contrast agent imaging parameters are set, data representing contrast agents is displayed on the display 20.

Figure 2:
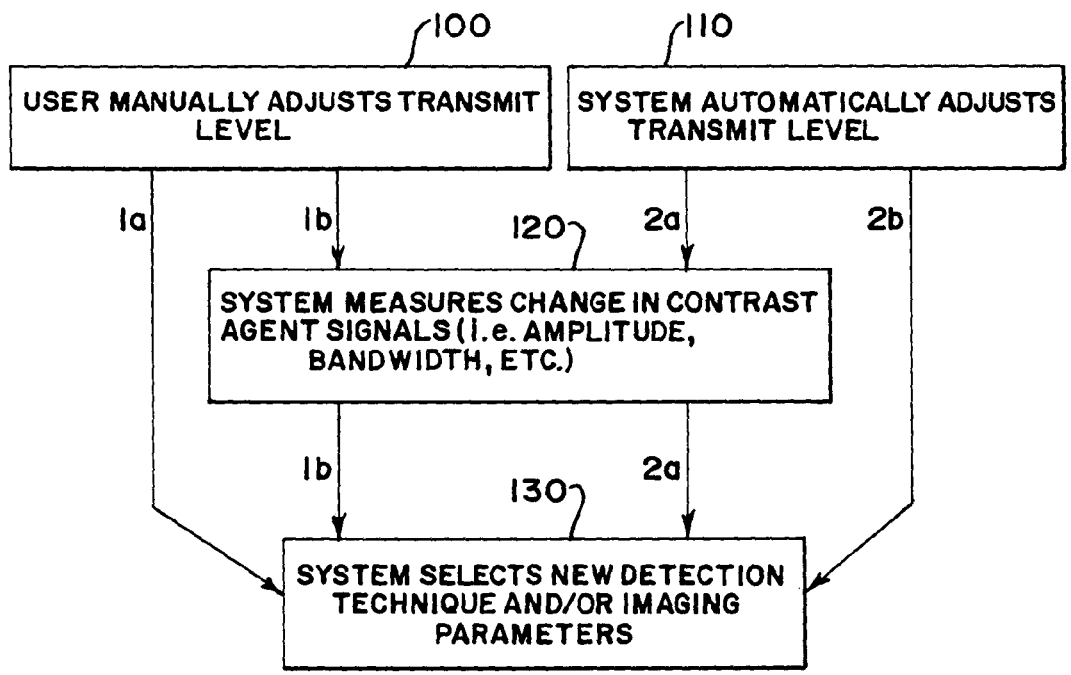
FIG. 2 is a flow chart diagram of one method for configuring parameters for contrast agent imaging.

FIG. 2 shows one embodiment of a method for setting parameters for contrast agent medical imaging. A contrast agent imaging configuration is provided on a medical diagnostic ultrasound system. For example, the user navigates through a menu structure to select a generalized contrast agent imaging configuration. The generalized contrast agent imaging configuration is not specific to a particular contrast agent imaging detection technique, so may be associated with two or more contrast agent detection techniques, such as techniques having different transmit sequences. Alternatively, the user selects one of several available contrast agent imaging configurations specific to a contrast agent detection technique. In response to the selection, the system is configured for contrast agent imaging.

In acts 100 or 110, a transmit level is set or altered. Where the system is being initially configured, the selection of the contrast agent imaging configuration assigns a transmit level or requests user entry or selection of a transmit level. During imaging, the user or the system alters the transmit level. Any of various ranges of settings may be provided. In one simplified embodiment, at least low, medium and high transmit levels are provided. Changing the "transmit level" includes any change to the transmitted signal that alters the delivered energy, peak amplitude, and/or the shape of the pulses. This level is typically adjusted as a monotonically increasing or decreasing function by the user. Examples include changes in amplitude, power, energy, and pulse/envelope shape. A change in the transmit level can also be programmed within an available "macro" to facilitate abrupt changes in the level with a single toggle or click. For example, a change from 5% to 100% of the maximum available transmit power is provided in response to a single action.

In response to the transmit level being set or altered, one of four pathways 1a, 1b, 2a and 2b are followed. Additional or fewer pathways may be used in alternative embodiments. In one embodiment, each pathway is available for a system or during an imaging session. In other embodiments, only one or a subset of pathways is available for a system, during an imaging session and/or in response to specific events. For example, where a system does not provide for automatic or measured adjustment of the transmit level, paths 1a and 1b are used. As another example, where a system does not provide for adaptive or measured determination of one or more contrast agent imaging parameters, paths 1a and 2b are used.

Paths 1a and 1b are responsive to the user setting the transmit level of act 100. In one embodiment, the user sets the transmit level by adjusting a single control, such as to alter the displayed image to a more desirable presentation. In additional or alternative embodiments, the paths 1a and 1b are responsive to the user setting the transmit sequence or contrast agent detection technique with a single control. For example, one control is used to adjust both the transmit level as well as the contrast agent detection technique through a range of possible combinations.

Paths 2a and 2b are responsive to the processor 18 automatically setting the transmit level or contrast agent detection technique in response to a measurement. A characteristic of received signals responsive to a current transmit level is measured. The transmit level setting is then selected as a function of the measured characteristic. In one embodiment, the system gain is also automatically set as a function of the selected transmit level. Any now known or later developed measurements may be used, such as disclosed in U.S. Pat. No. 6,899,681.

Act 120 is performed for paths 1b and 2a. After the transmit level or other initiating change (e.g., detection technique) is performed, one or more further measurements are performed. For example, the transmit level is altered and the system 10 automatically measures any change in response of the contrast agent. The amplitude, bandwidth, spectral response or other characteristic of the returned echoes is measured. The measurements are used as one or more additional sources of information for selecting contrast agent imaging parameters. Where act 110 is performed, one, some or all of the measurements of act 120 may be the same, so are not repeated in act 120. For example, the data from measurements of contrast signals to determine the new transmit level may also be used to select new contrast agent detection techniques and/or imaging parameters.

In act 130, the transmit level and/or any other measurements are used to select new contrast agent imaging parameters. The system 10 automatically selects a new contrast agent detection technique and/or imaging parameters based on preprogrammed options or the table. In one embodiment, the transmit level alone is used to determine one or more contrast agent imaging parameters. An alteration in the transmit level may result in a change of the contrast agent detection technique or may result in alteration of imaging parameters other than the detection technique. For example, as the user manually adjusts a transmit level, the system 10 automatically selects through a range of combinations of contrast agent detection techniques and other contrast agent imaging parameters based on preprogrammed options or the table.

Due to contrast agent behavior, tissue behavior, and system limitations, different contrast agent detection techniques and contrast agent imaging parameters dependent on the transmit level provide more optimal contrast agent imaging. With the goals of maximum sensitivity and maximum agent-to-tissue specificity, the contrast agent imaging parameters are changed as a function of different transmit levels. Various factors contribute to optimization in this way: contrast agent nonlinear behavior shows broadened frequency content with increasing pressure; contrast agents are disrupted and destroyed with increasing pressure; for low transmit level or low MI imaging where contrast agents are minimally destroyed, received signals are often near the system noise floor; tissue second harmonic generation due to nonlinear propagation increases with increasing pressure; front-end electronics may saturate more easily with larger signals from increased transmit levels; systems, inclusive of the transducer 12, may be nonlinear and increasingly nonlinear as signal levels increase; frame rates need not be maximized for high transmit level or high MI imaging, since contrast agents are destroyed at high MI and low frame rates are necessary to allow agent to reperfuse into the imaging plane; and at high transmit levels, thermal constraints may restrict the acoustic output pressures per unit of time.

In one embodiment of act 130, two or more transmit level settings are available to the user, such as a set of user-accessible options for the setting the transmit level. Settings for one, two, three or more contrast agent imaging parameters are associated with each of the transmit level settings. For example, the transmit level, the transmit sequence, the transmit modulation frequency and the receive demodulation frequency are set in response to an initial setting by the user. Each of the same parameters is then altered in response to a change in the transmit level, such as by adjustment of a single control by the user. In one embodiment, one control adjustment results alteration of a plurality of contrast agent imaging parameters. The setting of one or more of the contrast agent imaging parameters may be maintained even with a change in the transmit level or other parameters. For example, the transmit level is altered without altering the transmit sequence. In this example, the user adjusts the transmit level with the single user input control and various parameters are changed. A further adjustment may result in a change of the transmit sequence and associated detection technique.

Contrast agent imaging parameters include: transmit sequence, detection technique, transmit modulation frequency, transmit bandwidth, transmit coding, number of transmit foci per scan line, number of transmit pulses per scan line, number of transmitted lines per image, time between transmissions, velocity scale, reverberation-suppression pulses, receive bandwidth, receive demodulation frequency, pre-detection gains, and post-detection gains. Other now known or later developed contrast agent imaging parameters may be provided, set and altered as discussed herein.

The following table, Table 1, illustrates an example embodiment for act 130 where the system configuration changes based on three different transmit levels, "Low", "Middle", and "High". In this example, the low transmit level is associated with little or no destruction of contrast agent. The middle transmit level is associated with some but acceptable destruction of contrast agents while allowing substantially continuous imaging. The high transmit level is associated with likely contrast agent destruction or substantially maximum MI. The three levels may be set relative to different types of contrast agents, such as the low being appropriate for avoiding destruction of an easily destroyed contrast agent and the medium being appriorate for avoiding destruction of a more hardy contrast agent. In this example, the three levels are different transmitted acoustic peak pressures or different energy levels. For more than three transmit levels, simple interpolation between chosen configuration settings are adopted or unique values for each available transmit level are generated.

TABLE 1

|  | Low transmit level (e.g., 0.2 MI) | Middle transmit level (e.g., 0.75 MI) | High transmit level (e.g. 1.9 MI) |
| --- | --- | --- | --- |
| Transmit sequence | Multiple transmit pulses with interpulse amplitude and phase | Multiple transmit pulses with interpulse amplitude and phase modulation | Multiple transmit pulses with identical interpulse amplitude and phase |

TABLE 1-continued

|  | Low transmit level (e.g., 0.2 MI) | Middle transmit level (e.g., 0.75 MI) | High transmit level (e.g. 1.9 MI) |
| --- | --- | --- | --- |
| Transmit modulation frequency | modulation lowest | middle | highest |
| Transmit bandwidth | lower | high | high |
| Transmit coding | yes | yes | no |
| Number of transmit foci | Minimal | Minimal | Maximum |
| Number of transmit pulses per image line | Standard + extra | Standard | Standard |
| Number of scan lines per image | Lower | Lower | high |
| Directional estimates available | Optional | Optional | No |
| Extra inter-pulse/line/frame time | No | No | Yes |
| Scale (PRI) options | Yes | Yes | No |
| Reverberation-suppression pulses | Yes | Yes | No |
| Receive bandwidth | broad | narrow | broadest |
| Receive demodulation frequency | middle | large | small |
| Receive system gains | Maximize sensitivity | Maximize sensitivity | Minimize saturation |
| Image area automatic adjustment | If frame rate not achieved | No | No |

While many contrast agent imaging parameters are shown as having different values for the different transmit levels, more or fewer parameters may be changed. For example, for setting at or alteration to the low transmit level, the transmit sequence has multiple pulses with one or both of different amplitudes and phases. One or both of (i) the transmit modulation being low and (ii) the receive demodulation frequency being medium is also used. For setting at or alteration to the medium transmit level, the transmit sequence has multiple pulses with one or both of different amplitudes and phases. One or both of (i) the transmit modulation being medium and (ii) the receive demodulation frequency being high is also used. For setting at or alteration to the high transmit level, the transmit sequence has multiple pulses with all pulses having one or both of a same amplitude and a same phase. One or both of (i) the transmit modulation being high and (ii) the receive demodulation frequency being low is used. Other parameters may stay the same or be set in response to different information.

The transmit sequence is associated with or corresponds to the contrast agent detection technique. Two different transmit sequences, such as associated with CPS (see U.S. Pat. No. 6,494,841, the disclosure of which is incorporated herein by reference) and ADI (see U.S. Pat. Nos. 6,436,041 and 6,497,666, the disclosures of which are incorporated herein by reference) are provided in table 1. Other transmit sequences may be used for the same or different transmit levels. For example, higher transmit levels are assigned to transmit sequences and detection of: transmitting at least two pulses 180 degrees out of phase with a same amplitude along a same scan line, determining flow energy, detecting fractional harmonics, transmitting pulses adapted for contrast agent destruction with intermittent detection of contrast agents, and transmitting identical transmit pulses. Lower transmit levels are associated with one of: transmitting at least two pulses with different amplitudes along a same scan line, transmitting with different phasing as a function of scan line, transmitting at least two pulses with different phasing along a same scan line, and combinations thereof. Other groupings of transmit sequences and detection techniques as a function of transmit level may be used. In a further example, lower transmit levels are associated with power modulation, phase inversion, and power pulse inversion and higher transmit levels are associated with pulse inversion, power harmonics, ultraharmonics or similar transmit sequences and detection.

Each transmit sequence is defined, at least in part, by a number of pulses, a phase of pulses and an amplitude of pulses. For example, multiple transmit pulses are provided with interpulse amplitude and phase modulation (e.g., [0.5 −1 0.5]), with a same amplitude and phase (e.g., [1 1] or [1 1 1]), with interpulse amplitude modulation (e.g., [0.5 1 0.5] or with interpulse phase modulation (e.g. [1 −1] or [1 −1 1]). The transmit sequence is along one scan line. In alternative embodiments, one or more pulses of a sequence are along adjacent scan lines.

Interpulse amplitude and phase modulation allows detection of all nonlinear signals from contrast agents and proper receive filtering can suppress tissue signals and isolate contrast signals from tissue signals. This combination provides contrast signal sensitivity and specificity (see U.S. Pat. No. 6,494,841 showing an example of [0.5 −1 0.5]*[1 1 1]). For "Low" and "Middle" transmit levels, nonlinearities from the contrast agents are efficiently separated from the tissue and system linear and nonlinear components achieving excellent specificity. However at "High" transmit levels with interpulse amplitude modulation, agent-to-tissue specificity may decrease due to inefficient suppression of system nonlinearities and possible signal saturation. When transitioning from "Low" and "Mid" transmit levels to "High" levels, switching the transmit sequence to multiple identical pulses is preferred. For "High" transmit levels, multiple identical pulses maximizes sensitivity when proper "subtraction" filtering is applied to the receive signals as differences are efficiently detected when agent is disrupted (sees U.S. Pat. Nos. 6,436,041 and 6,497,666). An example [transmit]*[receive] sequence is [1 1 1]*[1 −2 1] where "*" is the convolution operator.

As transmitted levels increase, transmit system electronics may become increasingly nonlinear and receive electronics may saturate. Both of these types of nonlinearities are difficult to suppress while maintaining the sensitivity and the desired nonlinearities from the contrast agent signals. Transmit system nonlinearities may be similar, or identical, to the contrast signals since the transmit system nonlinearity signals are transmitted and linearly reflected by tissue. It is impractical to separate the two sources of nonlinearities, that from tissue or from contrast agents. For example, third order energy that exists in the fundamental frequency band that is typically generated by contrast agents at "Low", "Middle", and "High" transmit levels can be generated by the system at "High" transmit levels. Unequal receive saturation across multiple received pulses (most often showing up when interpulse amplitude modulation is used) from strong reflections from tissue may further destroy the expected rejection of strong tissue signals when selected receive interpulse filtering is applied. For example, a transmitted three pulse sequence with peak levels of [0.5 –1 0.5] and simple addition on receive should add to zero for linear tissue signals, however saturation of the second receive signal that is unequal to any saturation for the first and third pulse may adversly alter the rejection of linear tissue signals.

The use of multiple identical transmit pulses and proper receive interpulse filtering avoids the undesired system nonlinearities and effectively detects contrast signals for "High" transmit levels. Contrast signals are efficiently detected due to disruption, or destruction, through 'subtraction' interpulse filtering that detects differences between received pulses. System transmit nonlinearities are rejected as the nonlinearities are identical between the pulses and subtracted away on received. Receive saturation, if it exists, is typically consistent across pulses and is also rejected with interpulse filtering. Saturation can also be mitigated by applying reduced receive signal gains for "High" transmit levels.

By altering the transmit sequences, the associated contrast agent detection technique is also altered. In response to a change in a transmit level, the system 10 automatically adjusts from one contrast agent detection technique to a different contrast agent detection technique. Additionally or alternatively, different weights are applied to received signals as a function of alteration of the contrast agent detection technique. One contrast agent detection technique uses either or both of a different transmit sequence and a different receive weighting of received echoes than a different contrast agent detection technique. While table 1 shows using the same transmit sequence for both low and middle transmit levels, different transmit sequences and detection techniques may be used. Other transmit sequence factors may be altered while keeping the detection technique the same, such as using different amplitude modulation and/or phases as a function of the transmit level.

Another contrast agent imaging parameter is the transmit modulation frequency. Lower transmitted frequencies stimulate greater nonlinear behavior in contrast agents with currently available agents. Lower attenuation at lower frequencies also maintains signal quality compared to higher frequencies given a fixed transmit level or MI. For "low" transmit levels, lower transmitted frequencies may be preferred since operating conditions are often near the noise floor and the contrast agent signals are more nonlinear, offering greater signal returns. As transmit levels increase, there is benefit to increasing the transmitted frequencies given the sensitivity may improve due to higher acoustic pressures. Greater lateral spatial detail resolution is associated with higher frequencies. Also, greater axial spatial detail resolution may be available if the center of the passband of the transducer 12 and system 10 response is around the higher frequencies.

Another contrast agent imaging parameter is the transmit bandwidth. Although maximum transmit bandwidths are associated with the best axial resolution, more narrowband transmitted pulses increase the total energy without increasing peak pressures. For "low" transmit levels, contrast destruction is minimized so longer pulses (more narrowband bandwidth due to a greater number of cycles) improves the signal-to-noise levels. For higher transmit levels, the bandwidth is allowed to remain high by transmitting waveforms with a fewer number of cycles (e.g., 1–2 cycles) since stronger received echoes are available and more significant bubble disruption or destuction is acceptable.

Another contrast agent imaging parameter is the transmit coding. Coded excitation improves penetration and signal strength through transmitting longer pulses while maintaining the axial resolution associated with shorter pulses. Examples of methods for coded excitation are shown in U.S. Pat. Nos. 6,213,947 and 6,210,334, the disclosures of which are incorporated herein. Coded excitation may be useful for imaging contrast agents especially when "Low" transmit levels maintain signals near the noise floor. For higher transmit levels, contrast agents may distort the reflected echoes while the compression and rarefaction phases of the acoustic pulse excite the bubble, making coded excitation less useful. The decoding process through receive filtering may be less effective if the distortion is significant over the length of the excitation pulse. As an example, if a bubble was destroyed midway through the excitation pulse, the received echo would not be decoded properly, degrading the axial resolution. Coded excitation is more appropriate for "low" transmit levels and less appropriate for higher levels.

Another contrast agent imaging parameter is the number of transmit foci for each scan line and/or the number of scan lines per frame or image. To maintain high frame rates for real time "low" or "middle" transmit level imaging, the number of transmit foci is low, or minimal, as compared to for high transmit levels. For "low" and "middle" transmit levels, imaging with multiple pulses per image line is used as the transmit sequence. An additional set of transmitted pulses for each scan line results in further frame rate reduction. For "high" transmit level imaging, multiple transmit events that change the acoustic focus between any two events, or two transmit sets, may improve image uniformity and sensitivity. Since fresh agent must reenter the imaging plane between frames, the frame rates can be lower. Likewise, the density of scan lines within an image controls frame rate. Also, a lesser lateral density for low and/or middle transmit levels is less likely to destroy contrast agents. For high transmit levels, destruction of contrast agents may be desired.

Another contrast agent imaging parameter is the number of transmit pulses per image scan line or adjacent scan lines. The number of transmitted pulses per image line is defined by the transmit sequence as discussed above. The transmit sequence provides a "standard" or minimum number of pulses per scan line or adjacent scan lines. Additional pulses may be useful for extremely low transmit levels where minimal risk of destruction exists. For these levels, additional pulses can improve detectability with some loss in frame rates.

Another contrast agent imaging parameter is whether directional estimates, such as Flow mode velocity, energy and/or variance, are available. Directional estimates, such as velocity or directional energy (e.g., combination of velocity direction and energy) estimates, are selectively enabled based on the signal quality. Directional estimates are less accurate and poorly displayed when signal quality is poor as compared to simple energy estimates (i.e. no velocity information). "Low" transmit level imaging may not benefit from directional estimates given signals are often near the noise floor and estimates may be noisy. Also, "high" transmit level imaging may not benefit because significant destruction between multiple pulses can degrade signal estimates. Directional estimates are disabled for "low" transmit level imaging and "high" transmit level imaging by disallowing the display of directional estimates. This concept of enabling/disabling higher level statistical estimates based on transmit levels may also be applied to non-directional estimates, such as a variance estimate. These types of directional estimates may be enabled for "Low" transmit level imaging if coupled with more transmit pulses per image line or for higher transmit level imaging such as "medium" transmit level imaging.

Another contrast agent imaging parameter is the extra inter-pulse, line or frame time or delay. Adding additional time between transmit events reduces frame rates. However, additional power is more likely available due to added delay or lower duty cycles, improving sensitivity. For "low" and "middle" transmit levels, forcing lower frame rates may not be desired. However, lower frame rates are used for "high" transmit level imaging. When transducers are limited by thermal efficiency, additional cooling by delaying the next transmit, or set of transmits, may subsequently allow higher peak transmitted pressures. These delays are introduced between individual transmit events, between a set of events, and/or between individual or groups of frames. In one embodiment, the added delay corresponds to triggering with fixed offsets or triggering tied to an ECG signal. The ECG signal can minimize the number of transmit events, or images per heart beat, such as by triggering once or twice each heart beat.

Another contrast agent imaging parameter is the availability of scale and/or pulse repetition interval options. Acquisition of velocity information is allowed in addition to contrast agent detection for "low" transmit levels. Adjustment of the corresponding velocity scale is allowed. For the "high" transmit level, acquisition of velocity information in addition to contrast agent detection is prevented as contrast agent destruction at "high" levels may degrade accuracy of velocity estimation. Making different PRI and scale options available for "low" and "mid" transmit level imaging allows a range and strength of motion to be estimated with the use of contrast agents. A simple example is Color Doppler Velocity imaging or Color Doppler Energy imaging. These motion estimates can be simultaneously estimated and presented wit perfusion estimates by combining traditional Doppler transmit sequences with preferred contrast sequences (see U.S. Pat. No. 6,632,177, the disclosure of which is incorporated herein by reference). These single or multiple scale options, derived from the FRI options, are for detecting motion in addition to the perfusion level. For "High" transmit level imaging, increasing the time between successive transmit pulses per image line is not necessary as agents are easily disrupted with minimum PRIs based on desired imaging depths. PRI options are not available for "high" transmit level imaging. For high transmit levels, the range or strength of motion of contrast agents without additional motion information is provided.

Another contrast agent imaging parameter is the availability or use of reverberation-suppression pulses. Acoustic reverberation-suppression pulses preceed a desired transmit sequence to maximally suppress undesired energy, such a linear tissue signals. An interpulse receive filter combines the received pulses. For example, see the discussion in U.S. Pat. No. 6,436,041, the disclosure of which is incorporated herein. These types of pulses improve agent-to-tissue specificity and are more likely useful for "low" and "mid" transmit level imaging. For "high" transmit level imaging, reverberation-suppression pulses may unnecessarily destroy contrast before detection, so the reverberation-suppression pulses are not used.

Figure 3A:
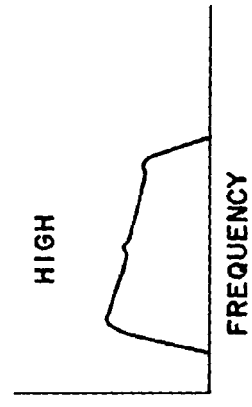
FIGS. 3a–c and 4 are graphical representations of various embodiments of received bandwidth spectra.
Figure 3B:
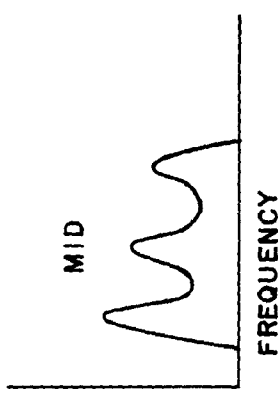
Figure 3C:
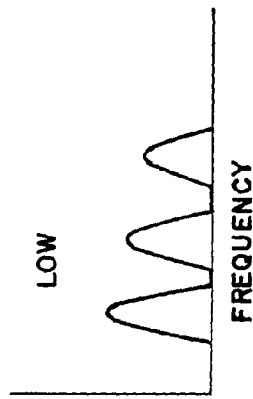

Another contrast agent imaging parameter is the receive bandwidth. Receive bandwidths are matched to the returned signals of interest. The receive bandwidth is controlled by one or multiple filtering, or similar, operations in the transducer and system signal pathways. Excited contrast agents are known to return broader frequency echoes with greater acoustic pressure. As an example, FIGS. 3a–3c show spectra returned from contrast agents up to the third order response. With sufficient transmitted bandwidths, the received echoes from multiple harmonic orders can coalesce into a spectra that effectively cover many harmonic orders with insignificant 'valleys' as shown in FIG. 3c. For "high" transmit levels, the receive bandwidth is best matched to this broad spectra including all the nonlinear information from the contrast agent. For "low" and "mid" transmit levels, the receive bandwidths may be narrower. Narrower bandwidths limit the amount of tissue second harmonics and maintain high specificity. As described earlier, non-identical multiple transmitted pulses are used for "Low" and "Mid" operating conditions. Some specific imaging sequences maintain second harmonic signals. An example of two [transmit]×[receive] sequences are [0.5 −1 0.5]*[1 1 1] and [0.5 1 0.5]*[1 −1 1] for use either with mid or low transmit levels. These two sequences maintain nonlinear fundamental (i.e., third harmonics in fundamental frequency band) as well as second harmonics. For "low" transmit levels, the second harmonics from tissue may be insignificant while the second harmonics from contrast agents may be substantial. For this scenario, the receive bandwidth is broad to capture nonlinear fundamental and some second harmonics since tissue signals do significantly reduce specificity. As the transmit levels are increased, the second harmonic from tissue becomes significant and can reduce specificity. For these "mid" transmit levels, the receive bandwidth is reduced, suppressing tissue second harmonics. The "high" transmit levels do not suffer from tissue second harmonics degrading the specificity since tissue signals are rejected through simple subtraction interpulse filtering after identical pulses are transmitted in one embodiment. As a result, the receive bandwidth is as broad as possible.

Another contrast agent imaging parameter is the receive demodulation frequency. Assuming received radiofrequency signals are demodulated down to baseband for further signal processing and filtering, different demodulation frequencies may be preferred for different transmit levels. As discussed above, the signals of interest span different frequency bands: "low"—mainly nonlinear fundamental with some second harmonics, "mid"—mainly nonlinear fundamental, and "high"—significant components from multiple orders including fundamental, second harmonics, third harmonics, fractional harmonics, and others. To increase the signal-to-noise ratio, the demodulation frequency centers the desired energy about the baseband. A smaller demodulation frequency for "high", a larger demodulation frequency for "mid", and a middle demodulation frequency for "low."

Another contrast agent imaging parameter is the receive system gains, including one or both of pre-detection and post-detection gains. For "low" and "mid" transmit levels, the system receive gains (e.g., pre-detection gains) are typically set up for maximizing sensitivity. However, these same gain settings may be too high for "high" transmit levels. Strong returned signals may saturate the electronics due to the high gains. To minimize saturation while maintaining adequate sensitivity, the gain values are lowered for "high" transmit levels. The variation in gain as a function of transmit level is linear or nonlinear. For example, the gain gradually reduces as the transmit level increases, but may more drastically reduce for very high transmit levels to avoid saturation.

Another contrast agent imaging parameter is the image area. Maximum frame rates are desired for real time "low" and "middle" transmit level imaging. However, other desired detection outcomes may produce unacceptable frame rates for large imaging areas. An automatic adjustment is performed or made available to provide frame rates at a specified or desired limit. This image area adjustment is in width, depth or a combination thereof.

Various considerations are weighed and/or counterbalanced for particular contrast agent imaging parameters of table 1. Other considerations may result in different settings for one or more of the transmit levels. Modifications, or alternatives, from this illustration are possible to enhance preferred considerations and for future capabilities. Different clinical imaging requirements may also indicate different alternatives, settings or considerations. As an example, high frame rates with excellent lateral resolution from high line densities may be desired. At high frame rates, low transmit levels are used to minimize agent destruction and image lines are formed from a single transmit event instead of image lines formed from multiple transmit events. To illustrate this alternative, the transmit sequence for "low" and "middle" uses a single transmit event. Second harmonic imaging may be the preferred imaging frequency on receive and the associated receive system parameters are set appropriately. The settings for the "high" transmit levels are the same, as high pressures destroy contrast agents. The frame rates are low so that new contrast enters the imaging plane.

The settings of table 1 are static or dynamic depending on one of four pathways as illustrated in FIG. 2. A static implementation uses a predefined set of configurations where each configuration is mapped to each possible transmit level. Pathways 1a and 2b from FIG. 2 represent the static implementation. A dynamic implementation uses real time or adaptive measurements of received signals to select an appropriate configuration for the selected transmit level. Any signal characteristic or multiple characteristics may be measured to decide which configuration is optimal.

In one example embodiment of the dynamic implementation, the "high" transmit level configuration is used initially to test for sufficient sensitivity. If sufficient sensitivity is available, a "high" transmit level configuration is adopted, otherwise a "low" transmit level configuration is adopted. For example, if no contrast agents are destroyed, the high transmit level configuration may return low or no value signals and a "low" transmit level configuration is preferred. If high value signals are detected over an area of interest, then sufficient sensitivity is provided and the "high" transmit level configuration is used. An example of a preferred "high" transmit level imaging technique is ADI using the [transmit]*[receive] sequence [1 1 1]*[1 −2 1]. This sequence rejects tissue flash due to abrupt movement and movement due to respiration and detects disrupted or destroyed contrast agents. A dynamic measurement, or test, for sufficient sensitivity using a preferred "high" transmit level imaging sequence is activated based on the user adjusting the transmit level or alternatively the system continuously or periodically tests for sufficient sensitivity without user intervention. While the overall configurations are selected in this example embodiment, the measurements may result in alteration of one or more parameters within a particular transmit level setting.

Figure 4:
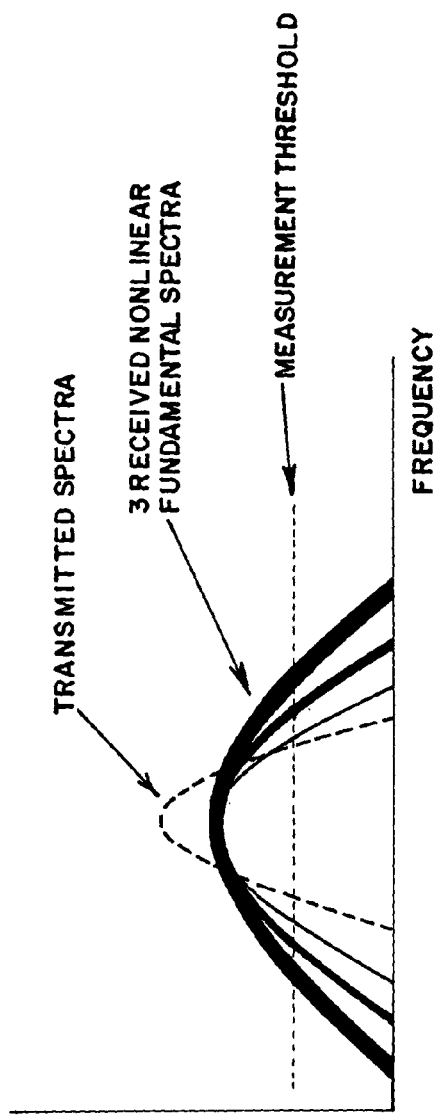

In another example embodiment of the dynamic implementation, a "low" transmit level configuration is used to measure the received signal bandwidth of nonlinear signals around the fundamental frequency band. Higher signal bandwidths map available configurations to those above the lowest transmit level configuration and below, or equal to, the highest transmit level configuration. As an example, the measured bandwidth can be compared to the transmitted bandwidth as shown in FIG. 4. Since the transmitted bandwidth is known, increases in the measured bandwidth indicate higher transmit levels are appropriate. A measurement threshold distinguishes the received bandwidth for each of the transmit levels. This measurement threshold is normalized to the peak signal for each measurement in one embodiment. The calculation of the received bandwidth can be performed in the time domain or frequency domain using current or future algorithms. As an example, Fourier analysis may be used for frequency domain analysis or zero-crossing detection may be used for temporal domain analysis. The nonlinear signals around the fundamental frequency are measured using one of several sequences. An example of two possible transmit sequences and associated detection techniques are [0.5 1 0.5]*[1 −1 1] and [0.5 −1 0.5]*[1 1 1]. Linear fundamental signals are suppressed and nonlinear fundamental signals are detected using these sequences.

Multiple measurements are made in one embodiment, but a single measurement can be used. The measurements are performed for a single scan line or for multiple scan lines in an image area. For multiple scan lines, the results are averaged together or otherwise combined to improve accuracy. For example, in an area of interest where sufficient contrast signals are detected, multiple received lines may be averaged together to reduce variations due to noise or inconsistent contrast agent concentrations. Multiple embodiments, like the two examples above, may also be combined to improve robustness and accuracy.

In one embodiment, the static implementation uses a "preset" functionality, such as the user selecting a general configuration or a configuration specific to a particular contrast agent detection technique. Clinical application presets allow the user to dial, or toggle, a control which puts the system into a predefined state. For example, a preset with a label, such as "High MI" configures the system 10 for using the ADI mode system parameters at a single transmit level (e.g., "high" transmit level settings of table 1). Upon selecting the preset control and pressing an activation key, imaging with ADI at a particular transmit level is provided. Adjustments in the transmit level result in continued use of ADI with one or more other contrast agent imaging parameters altered. Another adjustment in the transmit level switches to a different configuration, such as with a different contrast agent detection technique.

If a second preset control with a label such as "Low MI" is selected, the CPS configuration and settings at a single transmit level (e.g., low transmit configuration) are provided. Upon selecting the preset and activating imaging, contrast agent imaging with CPS is provided. In another embodiment, the user points and clicks or otherwise selects from a menu one of multiple "presets" options that deliver two or more different transmit levels for one or more contrast agent imaging detection techniques. For example, the user selects a preset associated with a type of contrast agent. Further refinement or optimization is then provided by automatically adjusting the transmit level and/or user adjustment of the transmit level.

Adjustment of transmit levels is provided if an initial selection is unsatisfactory to the user or measured to be incorrect. One or more adjustments of the transmit level result in using a different contrast agent detection technique. The same or different adjustments result in using the same technique but at a different transmit level. A single user control is used for both these alterations in settings. Other parameters than the detection technique are changed or remain the same in response to either of the adjustments in transmit level. At least three or more preset configurations are assigned to the single user control 19. For example, eight presets are defined that encompass contrast agent imaging parameters of the transmit sequence, transmit modulation frequency (Fm), receive system gain (Rg), and transmit power (TxPwr). Additional or fewer imaging parameters may be used. Table 2 provides one example using eight transmit level configurations:

TABLE 2

| Preset name | Sequence | Fm | Rg | TxPwr |
|---|---|---|---|---|
| A | [1 1 1] × [1 −2 1] | 8 | Lower | maximum |
| B | [1 1 1] × [1 −2 1] | 7 | standard | Minimum + 18 |
| C | [0.5 −1 0.5] × [1 1 1] | 6 | standard | Minimum + 15 |
| D | [0.5 −1 0.5] × [1 1 1] | 5 | standard | Minimum + 12 |
| E | [0.5 −1 0.5] × [1 1 1] | 4 | standard | Minimum + 9 |
| F | [0.5 −1 0.5] × [1 1 1] | 3 | standard | Minimum + 6 |
| G | [0.5 −1 0.5] × [1 1 1] | 2 | standard | Minimum + 3 |
| H | [0.5 −1 0.5] × [1 1 1] | 1 | standard | minimum |

In this example, the preset values A-H progress down in transmitted level and down in transmit modulation frequency where the values (1–8) and (+3 to +18) are not absolute numbers but symbols representing relative differences. An individual row in this table may also be used for a range, or subset, of available transmit power levels rather than changing for every transmit power level.

While the invention has been described above by reference to various embodiments, it should be understood that many changes and modifications can be made without departing from the scope of the invention. For example, the user control is a plurality of controls rather than a single control.

It is therefore intended that the foregoing detailed description be regarded as illustrative rather than limiting, and that it be understood that it is the following claims, including all equivalents, that are intended to define the spirit and scope of this invention.

We claim:

1. A system for setting parameters for contrast agent medical imaging, the system comprising:
a user input control;
a memory configured to store a table of a plurality of transmit sequences and a plurality of transmit levels, at least two transmit levels associated with at least one of the transmit sequences; and
a processor configured to select different ones of the plurality of transmit sequences and of the plurality of transmit levels in response to a single input from the user input control, the single input for adjusting a transmit level for contrast agent response during imaging, the processor configured to select, during the imaging, the different ones of the plurality of transmit sequences and of the plurality of transmit levels based on alteration of the transmit level received from the user input control, the selection corresponding to altering the transmit level without altering the transmit sequence for one of the adjusting of the transmit level and corresponding to altering the transmit level and transmit sequence for another of the adjusting of the transmit level, each transmit level being distinct and associated with one of the transmit sequences, and at least some of the transmit levels associated with a same one of the transmit sequences and at least some of the transmit levels associated with different ones of the transmit sequences.

2. The system of claim 1 wherein the user input control comprises a one of a rotatable knob, a touch screen control, and a button.

3. The system of claim 2 wherein the processor is operable to select from a range of transmit levels and at least two different transmit sequences in response to actuation of the user input control, a first of the at least two transmit sequences associated with lower transmit levels and a second of the at least two transmit sequences associated with higher transmit levels.

4. The system of claim 1 wherein the table includes settings for each of the transmit levels of transmit modulation frequency, transmit bandwidth, transmit coding, number of transmit foci per scan line, number of transmit pulses per scan line, number of transmitted lines per image, time between transmissions, velocity scale, reverberation-suppression pulses, receive bandwidth, receive demodulation frequency and combinations thereof.

5. The system of claim 1 wherein the processor is operable to obtain a measure of the contrast agent response and automatically select at least one of the different one of (i) the plurality of transmit sequences and (ii) of the plurality of transmit levels in response to the measure.

6. The system of claim 1 wherein each transmit sequence includes a number of pulses, a phase of pulses and an amplitude of pulses for each scan line.

7. The system of claim 1 wherein a first of the plurality of transmit sequences has multiple transmit pulses with interpulse amplitude modulation for each of a plurality of scan lines and a second of the plurality of transmit sequences has multiple transmit pulses having a same amplitude and phase for each of the plurality of scan lines.

8. A system for setting parameters for contrast agent medical imaging, the system comprising:
a user input control;
a memory configured to store a table of a plurality of transmit sequences and a plurality of transmit levels, at least two transmit levels associated with at least one of the transmit sequences; and
a processor configured to select different ones of the plurality of transmit sequences and of the plurality of transmit levels in response to a single input from the user input control, the single input for adjusting a transmit level for contrast agent response;
wherein the at least two transmit levels comprises at least three transmit levels, the at least three transmit levels being a low, a medium and a high transmit level, and wherein the processor is configured to select settings of:
for the low transmit level, the transmit sequence having multiple pulses with at least one of different amplitudes and phases, the transmit modulation being low and the receive demodulation frequency being medium;
for the medium transmit level, the transmit sequence having multiple pulses with at least one of different amplitudes and phases, the transmit modulation being medium and the receive demodulation frequency being high; and
for the high transmit level, the transmit sequence having multiple pulses with all pulses having one of a same amplitude and a same phase, the transmit modulation being high and the receive demodulation frequency being low.

9. The system of claim 1 wherein the processor is configured to select:
multiple transmit pulses with interpulse amplitude and phase modulation;

multiple transmit pulses having a same amplitude and phase;

multiple transmit pulses with interpulse amplitude modulation; or multiple transmit pulses with interpulse phase modulation.

10. The system of claim 1 wherein the processor is configured to set the transmit level as one of at least a low and a high transmit level, allow acquisition of velocity information in addition to contrast agent detection for the low transmit level, allow velocity scale adjustment for the low transmit level, and preventing acquisition of velocity information in addition to contrast agent detection for the high transmit level.

* * * * *